United States Patent [19]
Maria van Erp

[11] Patent Number: 6,102,891
[45] Date of Patent: Aug. 15, 2000

[54] BALLOON CATHETER WITH VALVE

[75] Inventor: Wilhelmus Petrus Martinus Maria van Erp, Leek, Netherlands

[73] Assignee: Cordis Corporation, Miami Lakes, Fla.

[21] Appl. No.: 09/232,208

[22] Filed: Jan. 14, 1999

[30] Foreign Application Priority Data

Jan. 16, 1998 [NL] Netherlands .......................... 1008051

[51] Int. Cl.[7] .................................................. A61M 29/00
[52] U.S. Cl. .............................. 604/96; 604/99; 604/920
[58] Field of Search ........................... 604/96–102, 912, 604/915, 920, 921, 246, 249, 256, 264; 606/191–194

[56] References Cited

U.S. PATENT DOCUMENTS 4,137,906   2/1979  Akiyama et al. .
4,643,712   2/1987  Kulik et al. .
4,646,742   3/1987  Packard et al. .
5,100,385   3/1992  Bromander ................................ 604/99
5,368,579  11/1994  Sandridge .
5,531,689   7/1996  Burns et al. .............................. 604/99
5,569,197  10/1996  Helmus et al. .

FOREIGN PATENT DOCUMENTS

WO 97/37714  10/1997  WIPO .

Primary Examiner—Glenn K. Dawson
Assistant Examiner—Michael J. Hayes
Attorney, Agent, or Firm—Michael W. Montgomery

[57] ABSTRACT

A balloon catheter has a tubular basic body with distal and proximal ends, defining a lumen extending between the ends, and a balloon near the distal end connected with the lumen, wherein the catheter has a maximum radial profile size corresponding to that of a guidewire. A controllable closing device or valve is arranged inside the inflation lumen which can selectively close off the lumen.

14 Claims, 5 Drawing Sheets

BALLOON CATHETER WITH VALVE

BACKGROUND AND SUMMARY OF THE INVENTION

1. Technical Background

The present invention relates to balloon catheters, and more particularly to a balloon catheter having a valve.

2. Discussion

Balloon catheters often have a flexible shaft, including a tubular basic body with a distal end and a proximal end, a lumen extending between the ends, as well as a balloon affixed to the shaft near the distal end that is connected with the lumen. Such a basic balloon catheter is generally known, whereby the dimensions of the balloon and the tubular basic body are selected such that the balloon catheter can carry out a therapeutic treatment.

Balloon catheters may often be used with a guidewire. Unfortunately, guidewires may tend to move, such as when a catheter is withdrawn over the guidewire in order to replace it with another catheter, and such displacement is undesired.

One of the objects of the invention is to provide a balloon catheter having a profile size similar to that of a guidewire. The present invention provides a narrow low profile balloon catheter, which can serve as a guidewire, over which another catheter or medical device can be passed and introduced. This second, "interventional" catheter can be used to carry out the actual desired treatment, such as angioplasty or deploying a stent.

The balloon catheter according to the present invention can be operated to wedge itself in between the internal walls of a body cavity or blood vessel. Thus, the present invention tends to ensure that emboli will not enter the blood stream, because they will be intercepted by the balloon. In addition, the balloon catheter of the present invention tends to exert no significant force that might cause the guidewire to move.

Moreover, the balloon acts in addition as a stop or distal safeguard, in the sense that an interventional catheter used for the actual treatment is resisted from advancing beyond the inflated balloon of the present invention. This balloon acting as a plug is deflated until reaching its destination, so that during transport to this site, the balloon does not hinder the insertion of the present balloon catheter.

These and various other objects, advantages and features of the invention will become apparent from the following description and claims, when considered in conjunction with the appended drawings.

BRIEF DESCRIPTION OF THE DRAWINGS

The invention will be explained in greater detail below with reference to the attached drawings.

DETAILED DESCRIPTION OF THE PREFERRED EMBODIMENT

The following description of the preferred embodiments of the present invention is merely illustrative in nature, and as such it does not limit in any way the present invention, its application, or uses. Numerous modifications may be made by those skilled in the art without departing from the true spirit and scope of the invention.

Referring to the drawings, a balloon catheter system is depicted, with one of the preferred embodiments of the present invention being shown generally at 1. The balloon catheter of FIG. 1 has an inflatable balloon 3, a relatively long and flexible tubular shaft 2, and a hub 26. The balloon 3 is affixed to the shaft 2 near a distal end of the shaft 2, and the hub 26 is affixed to the proximal end of the shaft 2.

In a balloon catheter according to an embodiment of the present invention, a controllable closing device or valve has been arranged inside an inflation lumen which can selectively close off the lumen. Such a closing device according to the present invention can have at least two functions. First, it can provide an opportunity to remove or purge, air present inside the balloon catheter prior to use, and then close off the balloon catheter. Second, it becomes possible to maintain the pressure in that section of the lumen connected to the balloon and in the balloon itself, while alternately separate interventional catheters employed for the actual medical treatment can be introduced and passed over the initial balloon catheter according to the present invention which can act as a guidewire.

In one embodiment, the closing device is near the distal opening, and the closing device may include a body made of a material impermeable to fluids, such as a highly absorbing material, positioned in front of the distal opening. While air is being removed from the lumen of the balloon catheter through the distal opening by means of a liquid column, the distal opening is closed off automatically by the closing device, as it permeable to air but not to fluids. For this purpose, a porous material may be used. When a highly absorbing material is used, the body will expand in order to close off the distal opening when the liquid reaches the body.

In connection with purging the catheter of air, it is preferably a property of the balloon catheter according to the present invention, that at least an opening has been arranged near either the distal end or the proximal end in the tubular basic body, through which air can be removed from the lumen through the opening before using the balloon catheter. This removal may be achieved by means of a liquid column, which is pushed up from the end opposite the end containing the opening, as a result of which the air is pushed out of the opening.

If the closing device has been arranged near the opening, it may be designed to close off the opening itself. Preferably, the active controllable closing device closes off the lumen at a position between the balloon and the proximal end of the tubular basic body. In this way the distal end of the lumen, which is connected with the balloon, is closed off from the proximal end. A proximal connector, or hub, may be arranged at the end, along which the pressure inside the lumen and consequently in the balloon can be increased.

Next, the closing device should close off the lumen, retaining the pressure inside the balloon. In this manner, the balloon may be kept under pressure while other interventional catheters used to carry out the actual medical treatment can be passed over the original balloon catheter and removed. If an opening for the purpose of removing air from the lumen has been arranged at the distal end, the closing device should be able to also close off this opening.

As an alternative, the closing device may be constructed as a valve of any suitable configuration, which can be controlled by means of pressure or a mechanical connection. Various types of valves may be used, including a ball valve, a snap connection, or a membrane having cuts which move apart when a certain threshold value of pressure is reached. This is preferably a direction opposite to the one where the balloon is positioned, whereby this threshold value is considerably higher than the one which can be exerted on the membrane by the pressure inside the inflated balloon and the corresponding section of the lumen.

A closing device in the shape of a valve may have two components, whereby the functioning of the valve depends on the positions of the components in relation to one another. The control of the valve is closely connected with the adjustability of these positions. Preferably, one of the valve components is formed by a portion of the tubular basic body, while the other valve component is a second body placed inside the lumen of the tubular basic body, which closes off the lumen or the opening in different axial or radial positions. The components are preferably movable in relation to one another in a rectilinear or rotary direction.

In addition, the valve may form a one-way valve like the example given above in the shape of a membrane comprising cuts. Other embodiments include a tilting plate inside the lumen placed at a certain angle, etc.

In the different drawing Figures, the same reference numbers have been used to indicate similar components of different embodiments of balloon catheters according to the present invention.

Figure 1:
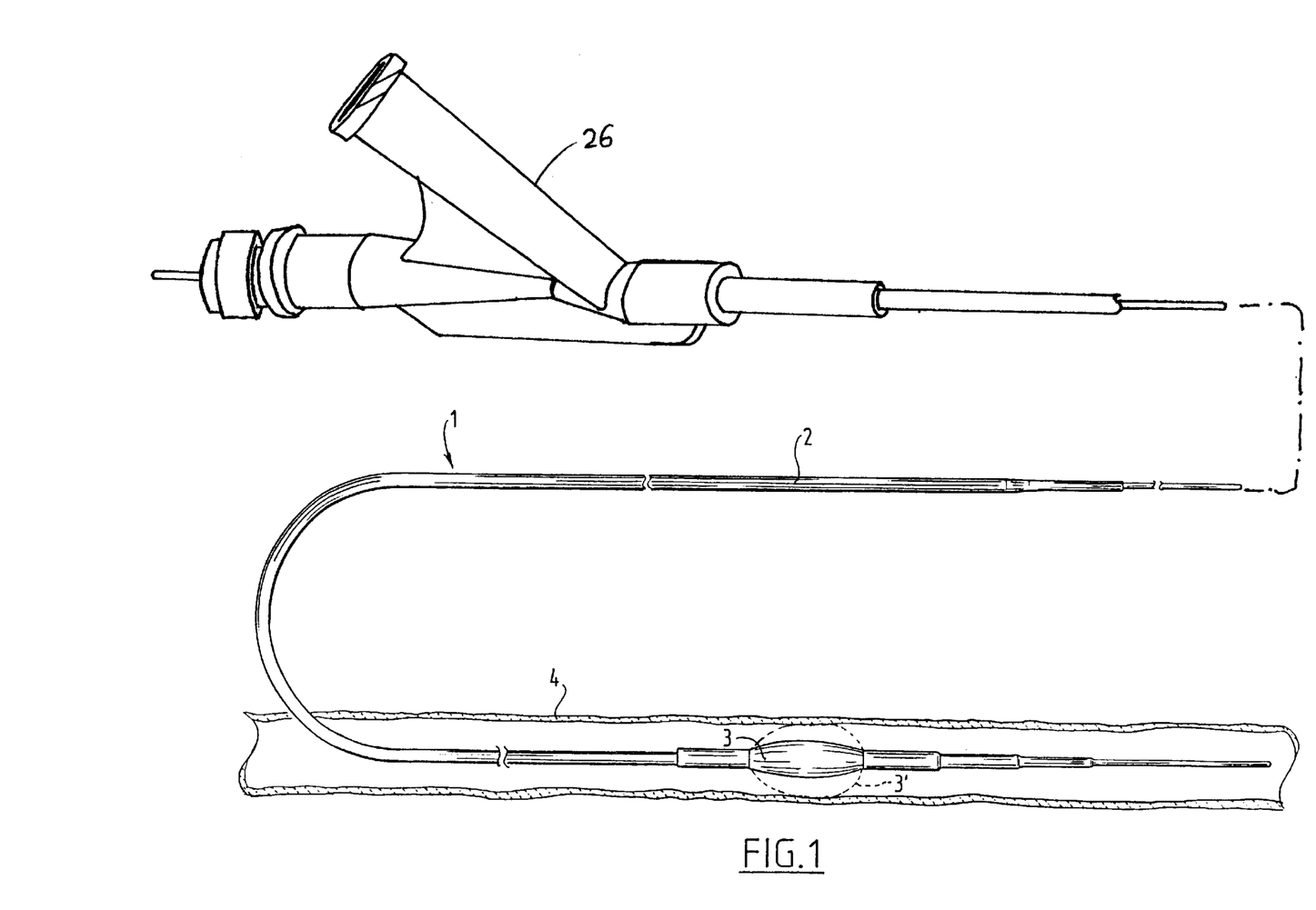
FIG. 1 shows schematically a balloon catheter according to the present invention in a position of use.

FIG. 1 shows a view of a catheter 1 which is one example of an embodiment of the present invention. The catheter 1 is depicted in a position of use in blood vessel 4, wherein the catheter has a tubular basic outer body 2, and a balloon 3 at the distal end of the tubular basic outer body. A lumen 5 extends between the proximal and distal ends of the tubular basic outer body, through which fluid under pressure can be pushed up from the proximal end of the tubular basic outer body 2 to the balloon 3. When fluid is conveyed to the balloon 3, the balloon 3 will tend to assume the inflated shape indicated with the dotted lines 3'.

A liquid should preferably be used for expanding the balloon 3, and not air or gas. The balloon catheter according to the present invention can be used in an artery, where the escape of air or another gas might be detrimental. Accordingly, liquid inflation fluid or radiopaque contrast media may be used.

Figure 2:
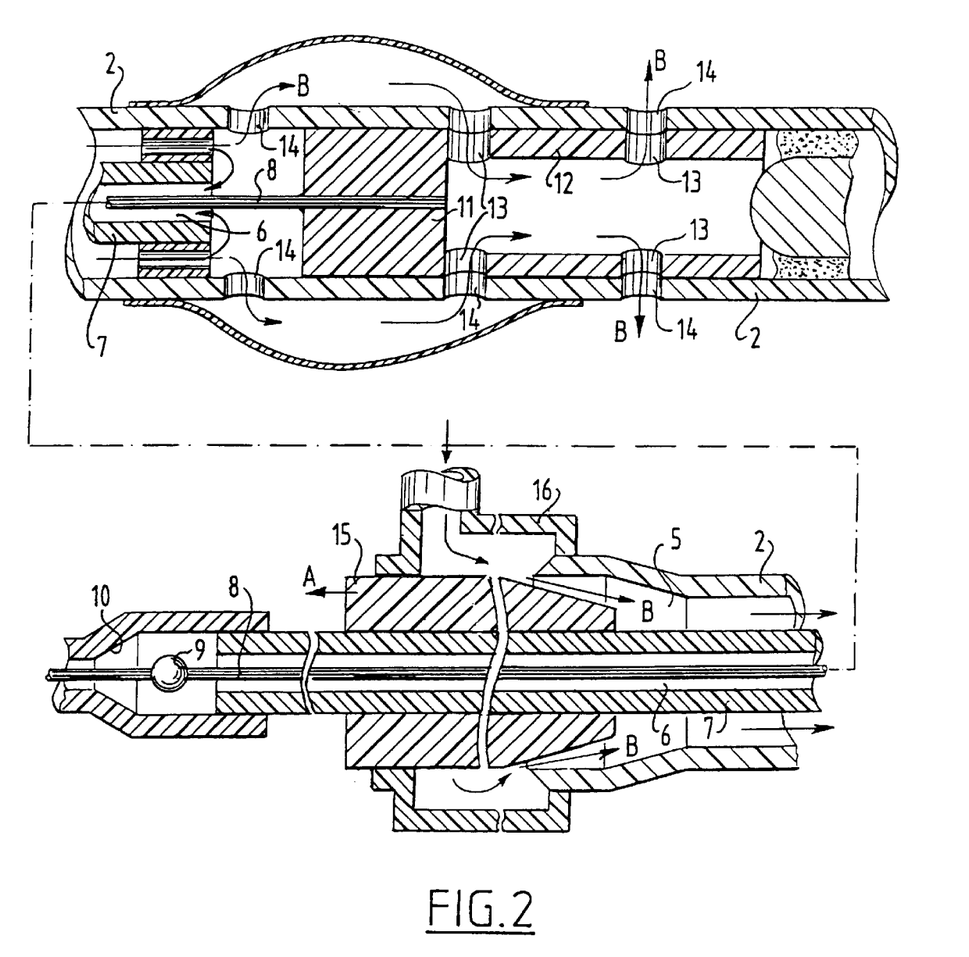
FIG. 2 shows a cross-sectional view of details of a balloon catheter according to the present invention, similar to the balloon catheter illustrated in FIG. 1.

Prior to using or introducing the balloon catheter, it may therefore be desirable to expel any air or gas present inside the lumen 5 of the tubular basic outer body 2 or the balloon 3. FIG. 2 shows a partial cross-sectional view of a balloon catheter similar to the catheter illustrated in FIG. 1. In the configuration illustrated here, the balloon catheter is capable of purging the system of air.

Inside the tubular basic outer body 2 is a tubular inner body 7 with a second lumen 6 running through it. The second lumen 6 contains a pull wire 8, which has a ball 9 at its proximal end near a hub 16 defining an internal narrowing chamber 10. At the distal end of the pull wire 8, a block 11 is provided near to the distal outlets of the first lumen 5 and the second lumen 6. A cylinder 12 having holes 13 is also connected to the block 11. In the situation illustrated here, the holes 13 are lined up with holes 14 in the tubular basic outer body 2, so that any air from inside the catheter can be removed through the holes 14 in the tubular basic body 2 situated outside the balloon 3. This purging operation of course should be conducted before the catheter is inserted within the body of the patient.

To this end, a slide 15 has been arranged at the proximal end of the tubular basic outer body 2, which is movable in the direction indicated by arrow A and back again, to close off the passage formed between the slide 15 and the proximal end of the tubular basic outer body 2. When the slide 15 has been moved in the direction indicated by arrow A, liquid can be introduced in the direction indicated by arrow B into the lumen 5 of the tubular basic outer body 2. Thus a liquid column is pushed up in the direction indicated by arrow B to the distal tip of the catheter, and air or other gases tend to be air removed through the balloon 3 and also through the second lumen 6 of the inner body 7. When the liquid exits at a proximal valve member, in this case a ball 9 at the proximal end of the inner body 7, air is thus removed from the catheter.

Next, the slide 15 may be moved again in the direction opposite to the one indicated by arrow A to meet the proximal end of the tubular basic outer body 2, as a result of which the flow of liquid is cut off. This situation has been illustrated in FIG. 3.

Figure 3:
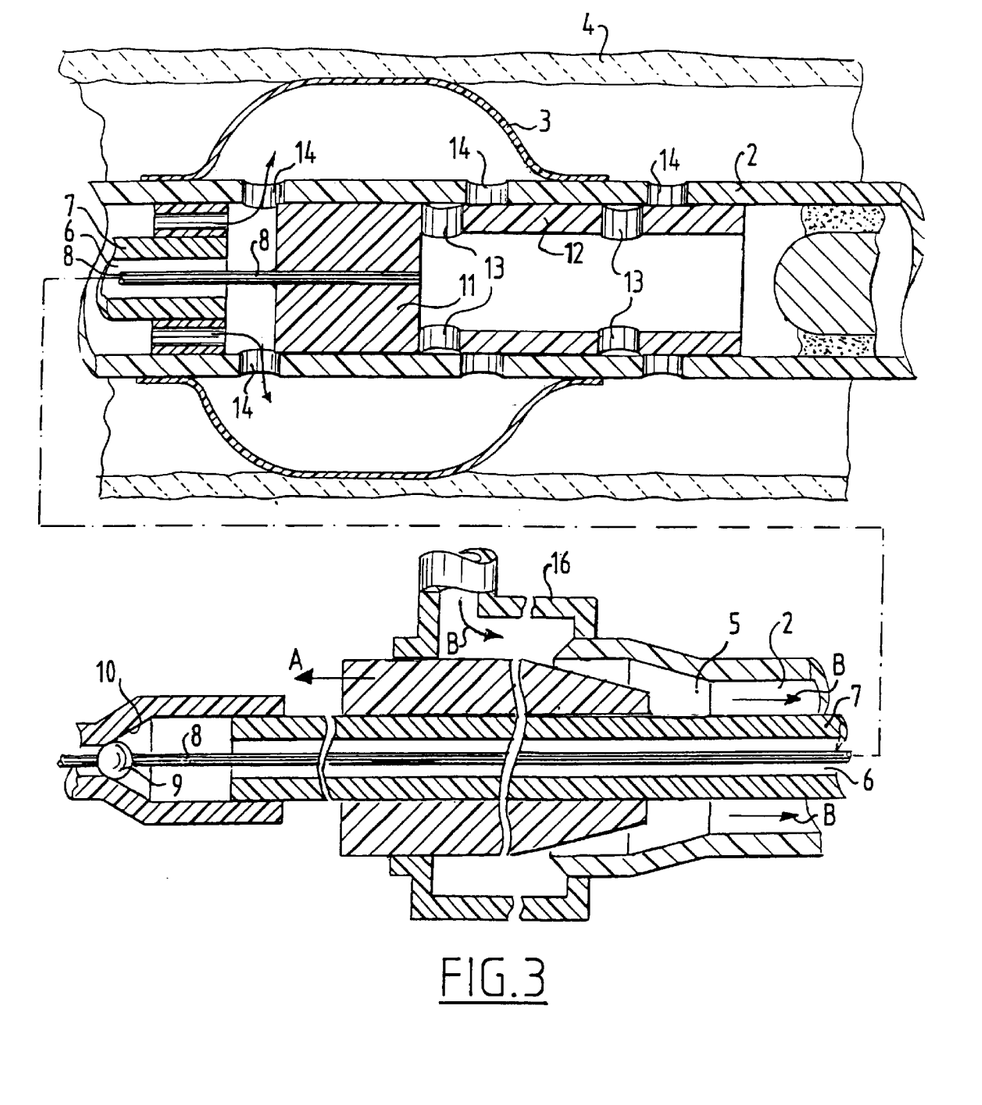
FIG. 3 shows a cross-sectional view of the balloon catheter corresponding to FIG. 2 in a second state of operation.

Incidentally, the flow of liquid in the direction indicated by arrows B is introduced via a connecting piece or proximal hub 16. The hub 16 may form an integrated part of the catheter or may be a separate unit connected in a detachable manner with the tubular basic outer body 2 and the slide 15 for the purpose of removing air or inflating the balloon.

The balloon 3 may be introduced and thereafter expanded in the manner illustrated in FIG. 3. To this end, the block 11 has been moved in the direction of arrow A, over such a distance that only the holes 14 in the tubular basic outer body 2 corresponding to the balloon are open. Thus a connection has been formed between the inside of the balloon 3 and the lumen 5, but not between the balloon 3 and the space or distal chamber created by the cylinder 12. The proximal ball valve 9 is in this case placed against the internal narrowing 10, closing off the lumen 6 at this point, so that no liquid can be discharged through it. This closes off the second lumen 6 of the tubular body 7, through which the fluid discharge flow might otherwise escape.

Also in this case, when the slide 15 has been moved in the direction of arrow A, liquid can be introduced into the lumen 5 of the tubular basic body 2 via the hub 16 in the direction indicated by arrow B. When the pressure in the balloon 3 has been increased sufficiently, the slide 15 may be closed again by moving it in the opposite direction, so that the pressure inside the catheter lumen 5 and consequently inside the balloon 3 is maintained.

Figure 4:
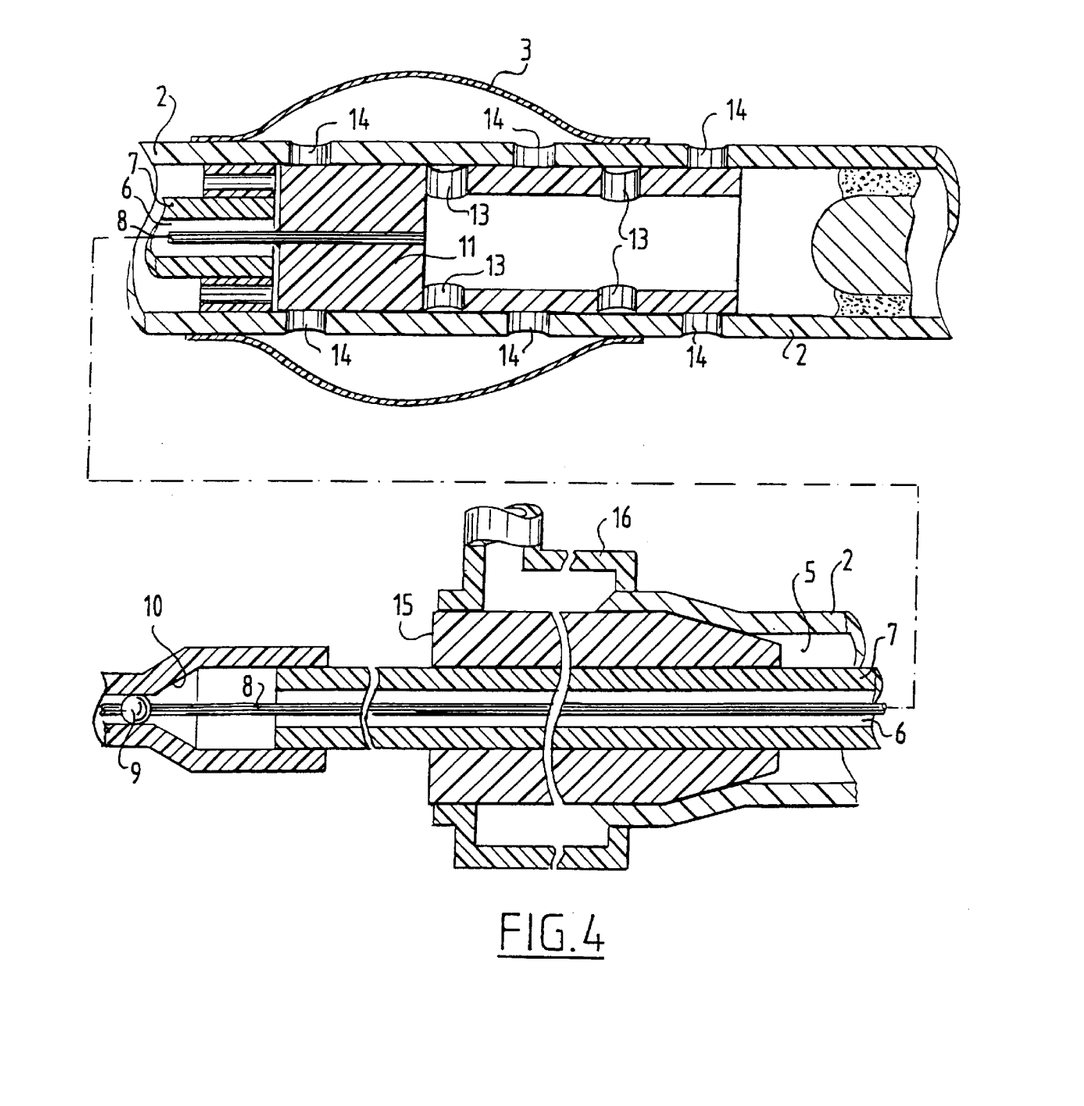
FIG. 4 shows a cross-sectional view of the balloon catheter corresponding to FIG. 2 in a third state of operation.

In the view illustrated in FIG. 4, the pull wire 8 has been pulled tighter in the direction of arrow A at the proximal end of the catheter, moving the block 11 further in a proximal direction, thus closing off all holes 14 in the tubular basic outer body 2.

In the state illustrated in FIG. 4, the balloon catheter according to the present invention is consequently capable of keeping the balloon hereof under pressure, without requiring the operator to maintain constant pressure. Both the lumen 5 of the tubular basic outer body 2, and the lumen 6 of the inner body 7, are then filled with liquid, and gas has been removed while the balloon is under pressure.

The ball 9 acts as a valve, just like the assembly of the block 11 and the cylinder 12. From the state illustrated in FIG. 4, the assembly of the ball 9, pull wire 8, and block 11 can be returned to the original position illustrated in FIG. 2 by introducing liquid under pressure into the lumen 5 in such a way that the block 11 is moved distally. As an alternative, a push rod may be used instead of the pull wire 8, in order to move the block 11 distally.

Figure 5:
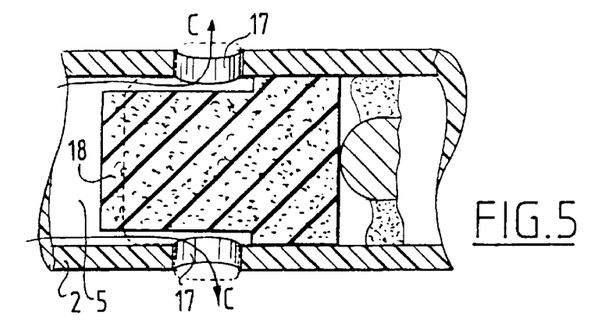
FIG. 5 shows a cross-sectional view of a detail of an alternative embodiment of a balloon catheter according to the present invention.

In the cross-sectional view in FIG. 5, a detail at the distal end of an alternative embodiment of a catheter according to the present invention is illustrated. Holes 17 in the tubular basic outer body 2 are used. A closing device may have been arranged at the distal end in a catheter comprising one lumen, or at the proximal end in a catheter comprising two lumens, in order to purge air or gas from the catheter. A plug or body 18 made of a strongly absorbing material may be positioned in front of the holes 17, while there is still some space in between the body 18 and the holes 17, through which air or gas can escape in the direction indicated by arrow C. When a liquid column, used for the purpose of removing gas and air from inside the catheter, reaches the body 18, this body 18 expands due to the liquid absorbed and closes off the holes 17. This happens automatically when the air/gas has been removed, as the liquid column only then should reach the body 18. As an alternative, a material may be used for the body 18 which is porous to air or gas but impermeable to liquid.

Figure 6:
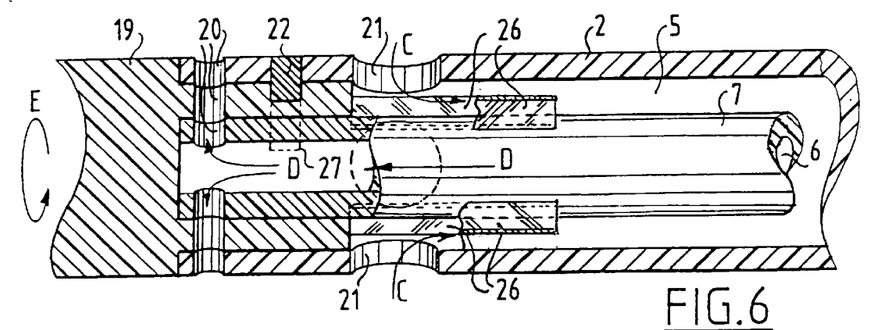
FIG. 6 shows a cross-sectional view of a detail of a second alternative embodiment of a balloon catheter according to the present invention.

In the cross-sectional view of FIG. 6, a detail of a third alternative embodiment of a balloon catheter according to the present invention is illustrated. A rotating handle 19 has been arranged at the proximal end of the tubular basic outer body 2. Also in this case, a tubular inner body 7 defining a second lumen 6 has been arranged inside the tubular basic outer body 2. The handle 19, the tubular basic outer body 2 and the tubular inner body 7 define holes 20 which, in the situation illustrated here, are in line with one another. The handle 19 has the shape of a block and includes grooves 26 its distal end, arranged in an axial direction, corresponding with the positions of passages 21.

When the distal end of the tubular inner body 7 is open and the distal end of the tubular basic body 2 is closed, then liquid entering the tubular basic outer body 2 via the passage 21 will tend to flow in the direction indicated by arrow C to the distal end, and return through the lumen 6 in the direction indicated by arrows D. Before the liquid exits through the aligned holes 20 in the direction indicated by arrows D, gas and air are removed from the catheter. Next the handle may be turned in the direction indicated by circular arrow E, as a result of which the holes 20 are no longer aligned but passages 21 remain in contact with the lumen 5, as the grooves 26 are at least twice as wide than the diameter of the holes 20. The liquid can no longer escape through the holes 20 but has removed air and gas from inside the catheter.

Next, the pressure inside the lumens 5 and 6 can be increased via the passages 21 which are still connected with one another. This is the case as the grooves 26 in the block-shaped handle 19 are at least twice as wide than the diameter of the holes 20, so that such rotation causes the holes 20 to no longer be aligned, and continues to maintain an open connection between the passages 21 and the lumen 5. This rotary movement in the direction indicated by arrow E is controlled by the stop 22, which, when turning the handle 19 in the direction indicated by arrow E, slides through a notch 27 placed in the outer surface of the block-shaped handle 19 and has been indicated with dotted lines. As the notch 27 extends in a radial direction over only a limited section of the outer surface of the block-shaped handle 19, also the maximum turn the handle 19 can make in the direction indicated by arrow E, is limited.

When the handle 19 has been turned so far that alignment of the holes 20 has just been interrupted, when there is still an open connection between the passages 21 and the lumen 5, the pressure inside the catheter can be increased and the balloon expanded via those passages 21.

In order to subsequently maintain the pressure inside the balloon, without keeping a supply of liquid under pressure in contact with the passages 21, the handle 19 may be turned further in the direction indicated by arrow E, so that sections of the block-shaped handle 19 will be positioned next to the grooves 26 in front of the passages 21, and the open connection between the passages 21 and the lumen 5 will be blocked. In this state, it is possible to pass and replace other catheters over the proximal end of a catheter according to the present invention illustrated here, without the pressure inside the balloon at the distal end being lost. Continuous treatment is therefore possible.

In the embodiment illustrated in FIG. 6, a rotary stepped slide has been employed. As an alternative, a stepped slide may be employed which is also translatable, or movable, in an axial direction. Both in the case of a translatable or a rotary stepped slide, it is possible to arrange indicators to indicate the current position of the stepped slide. Visual indications, such as markers, or a snap adjustment may have been employed, in which case the perception of a snap, either visual or sensory, indicates adjustment of the stepped slide.

It should be noted that the inner tubular body 7 is fixed to the inside of the block-shaped handle 19. Turning the handle 19 results in rotation of the tubular inner body 7. The span of the notch 27 is limited, so that as a consequence movement of the stop 22 is limited, and so is rotation of the internal tubular body 7. The stop 22, in conjunction with the notch 27 extending in a radial direction, resist the handle 19 being pulled from the inside of the tubular basic outer body 2 in an undesired manner in an axial direction. It is possible that the catheter may be formed of more than one assembly of a notch with a stop movable inside it, in order to disperse forces acting in an axial direction or radial directions.

Figure 7:
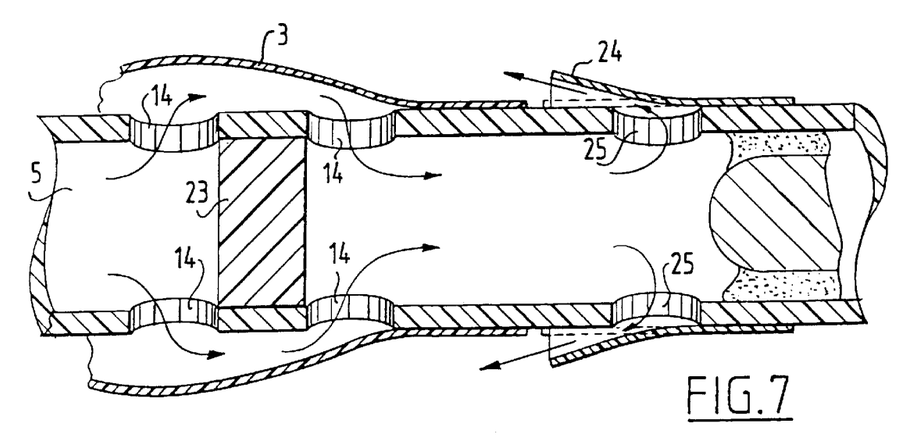
FIG. 7 shows a cross-sectional view of a detail of a third alternative embodiment of a balloon catheter according to the present invention.

In FIG. 7, a detail of another embodiment of a catheter according to the present invention has been illustrated. In this case, the lumen 5 of the tubular basic outer body 2 has been divided at the site of the balloon 3 by a partition 23, and holes 25 have been arranged in the tubular basic body 2 near the distal end of the balloon 3. The holes 25 are covered by means of a collar 24 which can move outward under the influence of a pressure being exerted from inside the lumen of the basic body 2, to allow air and gas to escape. As soon as liquid flows out of the holes 25, the pressure behind the liquid may be reduced, and the collar 24, made of an elastic material, will close off the holes 25. In this manner, all air and gas should have been removed from the catheter, and the open connection 25 with the exterior should have been closed off by means of a suitable closing device 24.

Closing off the lumen by the closing device may have one of two functions. First, a catheter filled with fluid from which all air and gas can be closed off have been removed. Second, pressure inside a balloon in an expanded state can be maintained, so that other activities may be carried out without having to pay special attention to the catheter.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A balloon catheter for performing a medical treatment on a patient, comprising:
    a flexible shaft, with a tubular basic body having distal and proximal ends, and defining an inflation lumen extending between the ends; the shaft defining a purge port;
    a balloon affixed to the shaft near the distal end, such that the balloon communicates with the inflation lumen; the balloon having an inflated state and a deflated state;
    a valve communicating with the inflation lumen, selectively operable between a first open position, a second intermediate position, and a third closed position; such that the valve in the open position allows fluid flow from the proximal end through the inflation lumen, through the balloon, and out the purge port to purge the catheter; the valve in the intermediate position partially closes to block fluid flow from inside the balloon to the purge port, while allowing fluid communication between the proximal end and the balloon through the inflation lumen to selectively inflate or deflate the balloon; and the valve in the closed position isolates the balloon by closing it off from the inflation lumen and the purge port, to maintain a constant pressure inside the balloon.

2. The balloon catheter as set forth in claim 1, wherein the shaft and balloon collectively define a maximum profile of 3 French size or less, such that the catheter can be used as a guidewire for additional medical devices.

3. The balloon catheter as set forth in claim 1, wherein the valve and the purge port are located near each another.

4. The balloon catheter as set forth in claim 1, wherein the valve and the purge port are located near to opposite ends of the catheter shaft.

5. The balloon catheter as set forth in claim 3, wherein the purge port is situated in a radial direction through the wall of the basic body, and the valve comprises a body which has been made of a material impermeable to liquids, positioned in front of the purge port.

6. The balloon catheter as set forth in claim 5, wherein the material is a strongly absorbing material.

7. The balloon catheter as set forth in claim 1, wherein the valve further comprises two valve components, such that the valve action between the first, second and third positions depends on the relative positions of the valve components in relation to one another.

8. The balloon catheter as set forth in claim 7, wherein one of the valve components is defined by a portion of the tubular basic body.

9. The balloon catheter as set forth in claim 7, wherein the valve components are movable in relation to one another in a longitudinal direction.

10. The balloon catheter as set forth in claim 7, wherein the valve components are movable in relation to one another in a rotary direction.

11. The balloon catheter as set forth in claim 1, wherein the valve is formed as a one-way valve.

12. The balloon catheter as set forth in claim 1, wherein the valve comprises a plug selectively closing off the inflation lumen.

13. The balloon catheter as set forth in claim 12, wherein the plug is connected to a pulling device which extends inside the inflation lumen, wherein the plug is movable in relation to the purge port.

14. The balloon catheter as set forth in claim 1, wherein the purge port is located distal of the balloon.

* * * * *

UNITED STATES PATENT AND TRADEMARK OFFICE
CERTIFICATE OF CORRECTION

PATENT NO : 6,102,891
DATED : August 15, 2000
INVENTOR(S): Wilhelmus Petrus Martinus van Erp It is certified that error appears in the above-identified patent and that said Letters Patent are hereby corrected as shown below:

On the title page, item:

[19] Maria van Erp

Should read:

van Erp

Signed and Sealed this

Seventeenth Day of April, 2001

Attest:

NICHOLAS P. GODICI

*Attesting Officer*   *Acting Director of the United States Patent and Trademark Office*